United States Patent [19]

Roberts

[11] 4,237,219

[45] Dec. 2, 1980

[54] RADIOIMMUNOASSAY ASSAY AND REAGENTS FOR MB ISOENZYME OF CK

[75] Inventor: Robert Roberts, St. Louis, Mo.

[73] Assignee: Washington University, St. Louis, Mo.

[21] Appl. No.: 846,095

[22] Filed: Oct. 27, 1977

[51] Int. Cl.³ .......................... C12Q 1/66; C12Q 1/50
[52] U.S. Cl. .......................................... 435/7; 435/17; 424/1; 424/1.5; 424/12
[58] Field of Search .............. 195/99, 103.5 A, 103.7; 424/1, 1.5; 435/7, 17

[56] References Cited

U.S. PATENT DOCUMENTS 4,067,775  1/1978  Wurzburg et al. ................. 195/99

OTHER PUBLICATIONS

Charles W. Parker, Radioimmunoassay of Biologically Active Compounds, Prentice-Hall Inc., pp. 93,94 and 126-132; 1976.

Millard N. Caroll et al., New Techniques in Tumor Localization and Radioimmunoassay, John Wiley & Sons, pp. 9-15; 1974.

*Primary Examiner*—Robert J. Warden
*Attorney, Agent, or Firm*—Grace J. Fishel

[57] ABSTRACT

Methods and materials for quantitative detection of MB and BB isoenzymes of creatine kinase by radioimmunoassay competitive displacement techniques involving antibodies to human BB isoenzyme which are specific for the B monomer, react with BB CK and cross-react with MB CK, but do not cross-react with MM CK. An acylating agent is employed to radioactively label purified CK isoenzymes used as antigens. Incubation is preferably carried out in a Tris buffer having a pH of about 7.4, in the presence of a suitable organic reducing agent such as mercaptoethanol.

15 Claims, 3 Drawing Figures

RADIOIMMUNOASSAY ASSAY AND REAGENTS FOR MB ISOENZYME OF CK

The invention described herein was made in the course of work under a grant or award from the Department of Health, Education and Welfare.

BACKGROUND OF THE INVENTION

The present invention relates generally to analyses for enzymatic substances and, more specifically, to methods and materials for the quantitative detection of BB and MB isoenzymes of creatine kinase by radioimmunoassay techniques.

Enzymes are proteinaceous substances produced by living cells. They function to bring about or accelerate chemical reactions in an organism without themselves undergoing marked chemical alteration in the process. One such enzyme, called creatine kinase, catalyzes an energy transfer (transphosphorylation) reaction, i.e., creatine + adenosine triphosphate ↔ creatine phosphate + adenosine diphosphate.

Creatine kinase enzyme is a dimeric molecule which exists in at least three combinative forms (isoenzymes), designated "MM," "MB" and "BB" on the basis of monomer combination. The M and B monomers which make up the enzymes each have a sulfydryl (SH) group-containing "active" site, the integrity of which is essential to catalytic activity. This active site is easily susceptible to inactivation upon contact with oxidizing materials. Each isoenzyme has a mass of approximately 82,000 daltons.

Analyses of profiles of creatine kinase isoenzyme (hereafter, "CK") activities in human tissue indicate that brain tissue ordinarily contains only the BB isoenzyme; skeletal muscle tissue ordinarily only the MM isoenzyme; and heart muscle tissue ordinarily both the MM and MB isoenzymes. Human plasma from normal subjects includes primarily the MM isoenzyme with less than 0.005 I.U. of MB CK per milliliter and no detectable quantities of BB CK.

After cerebral infarction, infection or other forms of cerebral damage, the concentration of MM isoenzyme in plasma is often somewhat elevated but the BB isoenzyme in plasma is generally not detectable. The lack of detectable BB CK is probably related to numerous factors including an effective blood/brain barrier. Damage to skeletal muscle by trauma or muscle disease such as muscular dystrophy is almost invariably accompanied by elevation of concentrations of the MM isoenzyme in plasma. Some very small increases in plasma BB activity have been reported in diseased muscle patients and immature muscle fibers of regenerating muscle have been proposed as the source of the BB in the blood.* Damage to heart muscle ordinarily results in elevation of plasma activity of both MM and MB CK.

*It has been reported that developmentally mature skeletal muscle may contain substantial quantities of BB CK which appears to be immunoreactive with a BB immune plasma but inactive when analyzed by cellulose acetate electrophoresis. [See, Armstrong, et al., J.Biol.Chem., Vol. 252, No. 10, 3105, 3112 and 3117 (1977).

Because the only human tissue containing appreciable amounts of MB CK is the myocardium, an elevation of MB concentration in blood—to the extent that it can be distinguished from increases in MM CK provides a remarkably sensitive and specific indicator of myocardial injury. Accordingly, analysis of serial changes in plasma MB CK has heretofore been employed to estimate the extent of acute myocardial infarction in experimental anaimals and human patients.

Analysis of a plasma sample for MB CK activity is frequently "indirectly" secured through prior art assays for enzyme activity. Employing a spectrophotometric technique for detecting NADPH developed from creatine kinase-catalyzed formation of ATP through coupled enzyme systems, relative increases or decreases in blood sample CK activity are predicated upon corresponding changes in catalytic activity of the enzyme isolated from the sample. The results of such prior art assays are directly dependent on several perameters, one of which is the rate of disappearance of the isoenzyme activity from plasma. Unfortunately, the factors responsible for disappearance of MB activity from the circulation have not been well elucidated. It is unclear, for example, whether disappearance of enzyme activity is ratelimited by inactivation, denaturation, or some form of removal of intact enzyme molecules from circulation. Consequently (and apart from the difficulty in distinguishing activity of MM CK from MB CK) activity-based determinations are subject to substantial unreliability.

The prior art provides certain proposals for radioimmunoassay ("RIA") analysis of plasma samples for use in quantitative detection of enzymes, and specifically creatine kinase isoenzymes, independently of analysis for enzyme activity. See, generally, the review article, "The Measurement of Enzymes by Radioimmunoassay" by J. Landon, et al. [Ann. Clin. Biochem., 14, pp. 90–99 (1977)] which recounts the relative superiority of RIA techniques to those based on catalytic activity. Simply put, according to one such RIA technique a stoichiometric excess of a pure, labelled (radioisotopic) material is allowed to associate (e.g., by antigen/antibody reaction) with the selected reactive substance such as antibody previously exposed to a sample containing an "unknown" quantity of enzyme which is unlabelled, but which is capable of a similar association. Direct quantitative information concerning the "unknown" concentration, as opposed to activity, is obtained on the basis of a count of radioactivity of the remaining selected substance which associates with the labelled material.

Nicholson et al., [Proc. Austral. Assoc. Neurologists, Vol. 10, pp. 105–108 (1973)] described a method involving labelling skeletal muscle MM creatine kinase with $^{125}I$ and report development of an RIA for the MM isoenzyme which assertedly measures "enzymes independently of the integrity of the active site." The method employed by Nicholson, et al. for labelling human creatine kinase is that described by Hunter, et al. [Nature, Vol. 194, pp. 4956 (1962)], employing chloramine-T to directly introduce the desired isotope into tyrosyl and histidyl residues of the enzyme protein chain. This method, however, has been associated with considerable structural changes (i.e., tertiary structure destruction) and loss of MM isoenzyme activity through disruption of the sulfhydryl-group-containing active site. Because the assay is assertedly specific for the M subunit, it invites cross-reaction with MM CK and MB CK and is thus incapable of distinguishing elevation of serum MB concentration resulting from myocardial infarction from elevation of serum MM concentration resulting from skeletal muscle damage or disease. The chloramine-T reagent used in the labelling procedure of Nicholson, et al. cannot be used for labelling the BB or MB isoenzymes due to their relative lability (instability, visa-vis MM) in the presence of the highly oxidative —sulfhydryl-group-disrupting— chloramine-T reagent. In sum, the Nicholson, et al. proposal has have not provided a useful basis to develop an RIA specific for BB and MB isoenzymes.

A prior art publication of interest to the background of the invention is Fang, et al. [*Biochem. Biophys. Res. Comm.*, Vol. 65, pp. 413–419 (1975)] which reports that creatine kinase enzyme activity losses from direct iodination by prior art chloramine-T, thallic trichloride and lactoperoxidase methods may be avoided through use, for iodination, of a Bolton-Hunter acylation reagent which conjugates (combines at a free amino ($NH_2$) group of the protein, thus avoiding disruption of the active site. The reagent involved was an iodinated compound derived from N-succinimidyl-3-(4-hydroxyphenyl propionate). Fang, et al. labelled rabbit skeletal muscle MM CK. There is no mention of human MM CK nor was there any mention of animal or human MB or BB CK isoenzymes. While the reported preservation of enzyme active sites would have suggested that a more accurate RIA for MM creatine kinase than that of Nicholson, et al. might be secured, the prior art was still without a method for labelling the more labile MB and BB CK isoenzymes. Furthermore, the antibody noted in Fang, et al. was to rabbit MM CK which offered no specificity for human BB or MB CK isoenzymes. The necessary ingredients for a human CK isoenzyme RIA with a specific antibody to BB and MB CK and the necessary stabilizing conditions for such analysis were yet to be developed.

BRIEF SUMMARY

The present invention provides methods and materials for accurate and extremely sensitive analysis, by RIA, of enzymatic materials. More specifically, the invention provides for quantitative detection of B subunit-containing (MB and BB) isoenzymes of creatine kinase and therefore permits, for the first time, the accurate determination of serum MB CK without either reliance upon kinase activity (ATP and then NADPH formation) or substantial interference by the MM isoenzyme as well as the accurate determination of tissue or blood BB CK. As such, the invention is expected to provide a most useful tool for the early diagnosis of myocardial infarction and for disorders which may involve release of BB CK into the plasma.

According to the invention, antibodies to human BB creatine kinase are obtained by immunization of rabbits with purified BB CK to provide serum containing antibodies which demonstrate specificity for BB and MB isoenzymes, but no cross-reactivity with the MM isoenzyme. Pure MB CK from myocardial tissue and/or BB CK from brain tissue is labelled with $^{125}I$ through use of a Bolton-Hunter acylating agent [e.g., N-succinimidyl-3-(4-hydroxyphenyl propionate)] to provide a reagent for competitive displacement binding RIA to ascertain concentration of MB or BB of a plasma or tissue sample. Incubation of BB antibody with labelled and unlabelled enzyme (antigen) is preferably carried out in an aqueous buffer comprising Tris at a concentration of from about 1.2 to about 2.0 M, and preferably 1.6 M, having a pH of from about 7.0 to about 8.0 and preferably 7.4. A preferred buffer also includes a suitable organic reducing agent such as mercaptoethanol in a concentration of from about 10.0 to about 30.0 mM, and preferably 20.0 mM, as well as standard agents such as gamma globulin and serum albumin for the prevention of non-specific binding. The buffer is believed to have substantial utility in preserving active site and tertiary structure as well as in retarding both undesirable "polymerization" caused by multiple reactions between antigen and antibody moieties and dissociation of reacted moieties. Separations from unbound (unreacted) reactants are carried out using ammonium sulfate to precipitate antibody associated with labelled and unlabelled antigen, because the unreacted materials have a substantially lower mass.

For purposes of indicating the background and/or illustrating the state of the art pertaining to the invention, applicant specifically incorporates by reference herein the disclosures of his jointly-authored publication entitled "Radioimmunoassay for Creatine Kinase Isoenzymes" appearing in *Science, Vol.* 194, pp. 855–857 (November, 1976), as well as the disclosure of the above-mentioned Landon, et al. article.

Further aspects and advantages of the present invention will become apparent upon consideration of the following detailed description and drawing wherein:

FIG. 1 graphically represents analytical findings concerning specificity of BB antibodies;

FIG. 2 graphically represents concentration-dependent competitive displacement of $^{125}I$ labelled MB CK by unlabelled isoenzyme; and FIG. 3 graphically compares results of practice of the invention to prior art practices.

DETAILED DESCRIPTION

Figure 1:
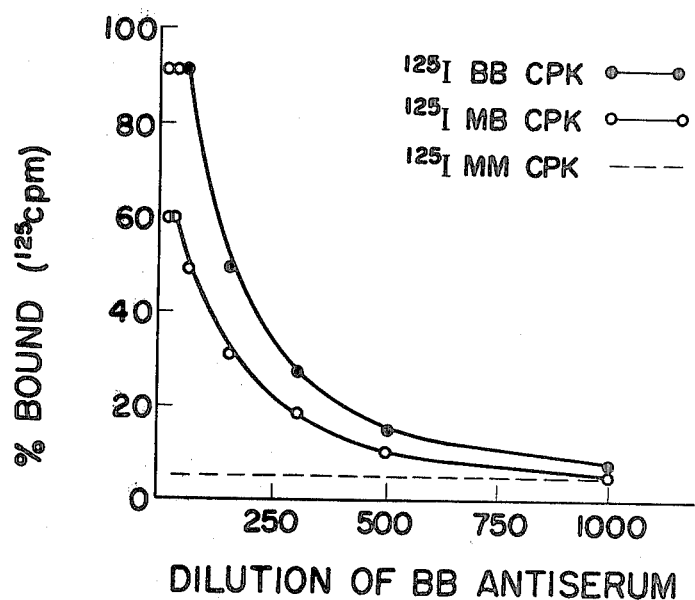

The following Examples illustrate practice of the invention and more specifically relate to (a) isolation of purified human CK enzymes for use in providing labelled enzymes; (b) labelling of CK isoenzymes; (c) preparation of antibodies to BB CK; (d) analysis of binding affinity and specificity of the antibodies; (e) general RIA procedures; (f) determination of MB CK in a plasma sample; and (g) methods and material for a typical clinical analysis for MB CK in a plasma sample.

EXAMPLE 1

Isolation of Purified Human CK Isoenzymes

MM and MB isoenzymes were prepared from human myocardium and BB from human brain obtained at necropsy within six hours of death. Homogenates from human myocardium and brain were prepared as follows. The fresh tissue was trimmed of fat, cut into small pieces with scissors and passed through a pre-cooled meat grinder. Ground tissue was homogenized in a Waring blender containing 20 g/ml of 0.5 M Tris-HCl [Tris(hydroxymethyl) aminoethane hydrochloride], pH 7.4, and 0.001 M 2-mercaptoethanol. All preparative procedures were performed at 0°–4° C.

The myocardial homogenate was centrifuged at 31,000 g for 15 minutes and the supernatant fraction filtered through 8 layers of cheesecloth. Ninety-five percent ethanol was added to the supernatant in dropwise fashion until the final concentration was 50%, and the mixture was allowed to stand while slowly stirring at 4° C. for 30 minutes. The precipitated material was removed by centrifugation and the supernatant fraction decanted. Again ethanol was added in stepwise fashion until a final concentration of 70% was obtained. The mixture was allowed to stand for 30 minutes and the resulting precipitate was recovered and saved. With the use of a homogenizer, the precipitated pellet was suspended in homogenizing medium equal in volume to 50% of the original homogenate. After centrifugation at 31,000 g, the pellet from this resuspended mixture was discarded and the supernatant fraction saved. To separate the MM CK, NaCl, 5 M, was added with rapid stirring to a final concentration of 0.05 M. DEAE Sephadex A-50 was then added (10 slurry for 48 mg of protein) and the mixture was stirred for 30 minutes. This suspension was filtered with a Buchner funnel lined with Whatman's No. 1 filter paper, and the filtrate was dialyzed against several changes of 0.01 M glycine, NaOH, pH 9.0, prior to freeze drying of the MM fraction. The MB CK present in the homogenate was adsorbed to the DEAE Sephadex previously added. Accordingly, after the MM filtrate had been obtained, the DEAE Sephadex was retained in the Buchner funnel and washed five times with 0.05 M Tris-HCl, pH 7.4, 0.05 M NaCl, and 0.001 2-mercaptoethanol. After the DEAE Sephadex had been washed, MB CK was eluted with Tris-HCl, 0.05 M, pH 7.4 containing 0.3 M NaCl. The eluate was dialyzed with glycine buffer, and then freeze-dried to obtain the MB fraction. To further enrich the MM and MB fractions, further ethanol fractionation and column chromatography was performed followed by dialysis, freeze-drying and storage at 0°–4° C.

CK was extracted from brain in the same fashion as from myocardium with the following exceptions. The final concentration of ethanol was 60% rather than 50%. After filtration to remove any potential MM fraction, Sephadex retained in the Buchner funnel was washed five times with Tris-HCl buffer containing 0.1 NaCl, and subsequently washed once with buffer containing 0.3 NaCl. BB CK remained adsorbed to Sephadex under these conditions and was then eluted with Tris buffer containing 0.4 M NaCl dialyzed against 0.01 M glycine, NaOH, pH 9.0, and freeze-dried.

Polyacrylamide gel electrophoresis [per Anido, et al., *Am. J. Clin. Path.*, Vol. 61, p. 599 (1974)] of the human preparations indicated that each isoenzyme was obtained in a sample devoid of activity attributable to other isoenzymes in the initial extract. MM CK averaged 392 IU/mg of protein, MB 46 IU/mg, and BB 110 IU/mg. Specific activity of the isoenzymes was increased by more than one hundred-fold over that present in the initial extract and analysis by SDS gel electrophoresis [per Weber, et al., *J. Biol. Chem.*, Vol. 244, p. 4406 (1969)] with staining for protein showed only one faint contaminating band of the MM, no contaminating bands of BB, and two very faint contaminating bands of the MB, indicating that the preparations were probably more than 90% pure.

EXAMPLE 2

Radioactive Labelling of CK Isoenzymes

Radioiodine ($^{125}$I) was utilized to radioactively label CK isoenzymes for subsequent use in a competitive displacement radioimmunoassay. To avoid exposing the enzymes to oxidizing agents and contaminants in the radioiodine, the $^{125}$I was first incorporated into N-succinimidyl ester 3-(4-hydroxyphenyl propionate) which in turn was reacted with amino groups on the CK isoenzyme protein. Radioiodination was performed by the method of Bolton and Hunter, supra, carried out at room temperature (23° C.) N-succinimidyl 3-(4-hydroxyphenyl propionate) (0.3 mcg) was treated with 5 millicuries (10-20 ul) of Na$^{125}$I, 50 mcg of chloramine-T and 10 μl of 0.25 M phosphate buffer, pH 7.5. The reaction was immediately terminated by the addition of 120 mcg of sodium metabisulfite in 10 μl of 0.50 M phosphate buffer, pH 7.5 containing 200 mcg of KI. The iodinated product was extracted into benzene (0.300 ml×2 portions) and recovered by evaporation of the solvent under vacuum. The addition of dimethylformamide (5 μl) before adding the benzene was necessary for full extraction of the ester into the solvent. The residue was used to label CK isoenzymes. The labelled residue was combined with 2–8 mg of MM, MB or BB CK in 1–2 ml of 0.01 M Na-borate buffer, pH 8.5. After gently shaking the reaction, for four hours at 4° C., the labelled isoenzymes were then dialyzed against the same buffer containing 0.0005 M 2-mercaptoethanol. Radioactivity per mcg of labelled CK isoenzymes averaged 200,000 cmp for MM CK and MB CK and 100,000 cpm for BB CK. The maximum loss of enzyme activity resulting from labelling and dialysis was less than 5% for each isoenzyme preparation.

EXAMPLE 3

Preparation of Antibodies to CK Isoenzymes

Utilizing the purified human MM and BB CK mixed with equal volumes of Freund's complete adjuvant, antibodies to CK isoenzymes were induced in rabbits. Initially, the rabbits were injected subcutaneously with 1 mg of immunogen (0.25 mg/foot pad). Subsequently, they were injected with 0.25 mg weekly for three weeks. All animals were given booster injections of 0.1 mg in complete adjuvant at monthly intervals thereafter. Ten days after each booster injection, the animals were bled and their serum analyzed for antibody activity. Ouchterlony agarose plates, prepared with BB antiserum exhibited single precipitant lines to BB and MB antigen but no precipitant line to MM. Plates prepared with MM antiserum exhibited a single precipitant line to both MB and MM but none to BB. Thus, antibodies to BB CK reacted with BB CK and also cross-reacted with MB but did not cross-react with MM indicating that it was specific for the B subunit. Similarly, MM antibodies were specific for the M subunit.

EXAMPLE 4

Binding Affinity and Specificity of Antiserum

The binding affinity and specificity of the BB and MM antibodies (rabbit antiserum of Example 3) was determined over a wide range of concentrations of the antibody by diluting the appropriate antiserum over a range of 1:15 to 1:1000. All determinations performed in duplicate were carried out in 12×75 mm glass tubes containing 1.6 M Tris buffer, pH 7.6, (200 ul) 2% bovine serum albumin (100 μl), 0.020 M mercaptoethanol (10 μl), 5 picograms of rabbit gamma globulin (50 μl). As noted earlier, the gamma globulin and serum albumin are believed to minimize nonspecific binding and the high concentration of Tris and 2-mercaptoethanol is believed to protect the sulfhydryl groups of the isoenzymes and prevent dissociation into monomers. To this mixture was added the appropriate dilution of antiserum in volumes ranging from 100 μl to 5 μl (dilutions performed with normal rabbit serum). $^{125}$I-labelled MM (0.1 mcg), MB (0.1 mcg), and BB CK (0.2 mcg) were added such that approximately 25,000 cpm were present in each tube. The total volume was kept constant at 500 μl with necessary adjustments being made with Tris buffer. The solutions were then incubated and gently shaken at 4° C. for six hours. Appropriate controls were incubated containing normal rabbit serum rather than rabbit antiserum.

Following the incubation period, separation of free from antibody bound labelled CK was accomplished by the addition of cold saturated ammonium sulphate with a final concentration of 44%, and allowing the solution to sit at room temperature for 15 minutes. The solution was then centrifuged at 2,000 g for 20 minutes, the supernatant decanted, and the pellet washed with 50% ammonium sulphate (400 μl) and again centrifuged. The pellets were counted in a gamma counter (Micromedic Systems, Inc.) until a minimum of 10,000 counts were obtained. The $^{125}I$ counts present in the pellet expressed as a percent of the total number of counts initially present represent percent binding. To optimize conditions for any possible cross-reactivity between the BB antibody and MM CK and vice versa for the MM antibody, determinations were done in which BB antiserum diluted only 1:15 was incubated with 4 mcg of $^{125}I$ MM and MM antiserum in a dilution of 1:15 with 4 mcg of $^{125}I$ BB.

Results of binding experiments using serial dilutions of BB antiserum from 1:15 to 1:1000 incubated with iodinated MM, MB and BB CK are shown in FIG. 1. Ninety-three percent of the $^{125}I$ BB was recovered in the pellet in dilutions of 1:30, but binding diminished rapidly with only 7% at 1:1000, demonstrating that binding was dependent on antibody concentration. Maximum binding of $^{125}I$ MB CK (60%) occurred at 1:15 dilutions but again binding was dependent on the concentration of antibody with only 5% binding at 1:1000 dilution. In contradistinction, $^{125}I$ MM exhibited no such antibody concentration dependent binding and at all dilutions was the same being between 3–5% which is the same as that of control (normal rabbit serum). These results demonstrated the antibody is specific for the B sub-unit rather than the molecule as a whole.

Results of binding with MM antiserum showed 94% binding of $^{125}I$ MM and 56% binding of $^{125}I$ MB and dilutions of 1:30. Again binding was dependent on the concentration of antibody and returned to control levels at a dilution of 1:1000. No specific binding was seen between the MM antiserum and $^{125}I$ BB. The MM antiserum exhibited specificity for the M subunit but no cross-reactivity with the B subunit.

EXAMPLE 5

General Procedure for Radioimmunoassay

To develop a competitive displacement radioimmunoassay for plasma MB CK, BB antiserum was used and the specificity of the BB antiserum for B subunits further established by comparing the ability of unlabelled BB, MB and MM CK to inhibit $^{125}I$ BB binding. The reaction was performed in the same buffer solution used for the binding experiments, but with the exceptions that the dilution of antiserum was kept constant at 1:150 and the amount of $^{125}I$ BB CK was kept constant at 0.2 mcg containing approximately 25,000 cpm. The antiserum dilution of 1:150 was chosen since this concentration of antibody binds about 50% of the $^{125}I$ BB [See generally, Parker, C. W., "Radioimmunoassays" in *Progress in Clinical Pathology*, Volume IV (Grune and Stratton, Inc., New York, 1974)]. A known amount of unlabelled BB, MB or MM CK was diluted from 1:15 to 1:1000 and incubated for six hours with $^{125}I$-labelled BB. Following incubation, the ammonium precipitated pellet was washed, centrifuged and counter for $^{125}I$ radioactivity. To further determine the specificity of unlabelled BB or MB to displace $^{125}I$ BB binding in the face of MM CK, inhibition curves were determined for MM incubated with BB or MB in which MM was present in a 25,000-fold excess over that of unlabelled BB or MB.

Figure 2:
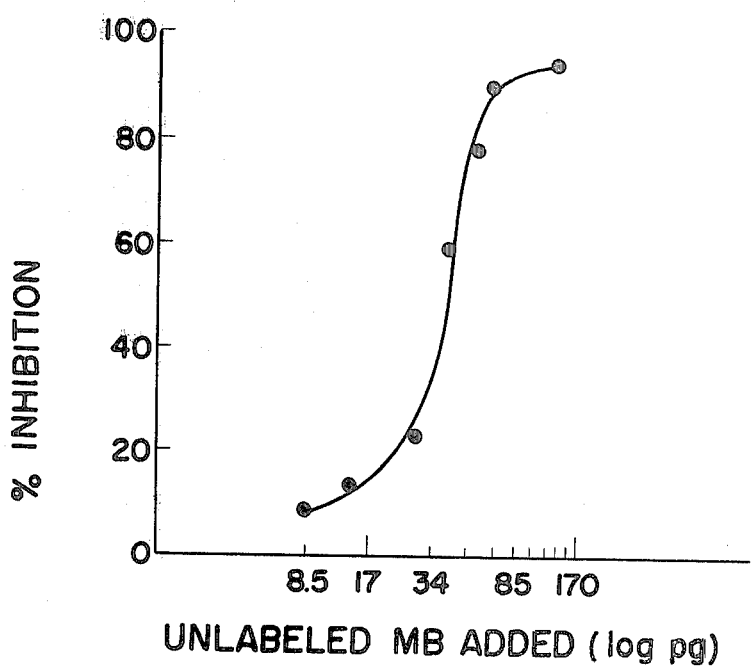

Unlabelled MB CK competitively displaced labelled BB CK from binding to the BB antibody which was dependent on the concentration of MB CK as shown in FIG. 2. The inhibition curve is steep between 17–80 pg/ml with 50% inhibition at 51 pg and complete inhibition of binding at a concentration of 80 pg/ml and above. A similar inhibition curve was seen for unlabelled BB which showed 50% inhibition at 26 pg/ml and complete inhibition at 125 pg/ml and higher. Unlabelled MM CK showed no inhibition of $^{125}I$ BB binding, even at 5 mcg/ml (2000-fold excess over $^{125}I$ BB CK). Furthermore, the competitive inhibition of unlabelled MB CK was unaltered in the presence of high concentrations of MM CK (5000 M excess over that of MB CK). Thus, the BB system as a competitive displacement assay for MB is extremely sensitive, detecting reliably a concentration of 20 pg/ml which in terms of enzymatic activity is $1 \times 10^{-6}$ IU/ml. Furthermore, the specificity is such that it detects at this level of sensitivity even in the presence of a 5000 molar excess of MM. Results of radioimmunoassays performed on heat inactivated serum constituted with known amounts of MB CK ranging from 20 pg/ml to 2 mcg/ml deviated by less than 3% from that expected.

EXAMPLE 6

Determination of MB CK in Plasma Samples

To determine the amount of MB CK present in an unknown sample, a standard MB inhibition curve is run with known amounts of unlabelled MB CK ranging from 2,000 to 20 picograms (pg)/ml of MB CK. The unlabelled MB CK is incubated with a constant amount of antiserum and $^{125}I$ BB CK as outlined previously under radioimmunoassay procedure. Serial dilutions (3–4) of the unknown sample are made and the amount of inhibition determined at each dilution and compared to the standard curve from which it is possible to calculate the amount of MB CK present expressed as ng/ml. To determine the accuracy of the assay, known amounts of human unlabelled MB CK were added to heat inactivated serum and serial dilutions done and results expected compared to that obtained. Plasma samples were obtained from five patients with acute myocardial infarction. At least 15 samples were obtained serially from each patient over a period of 48 hours. All samples were performed in duplicate and compared to enzymatic activity obtained by a kinetic fluorometric assay previously described in Roberts, et al., Am. J. Cardiol., Vol. 33, p. 650 (1974). All determinations for total CK enzymatic activity were done according to the method of Rosalki, S. B., J. Lab. Clin. Med., Vol. 62, p. 696 (1967).

Figure 3:
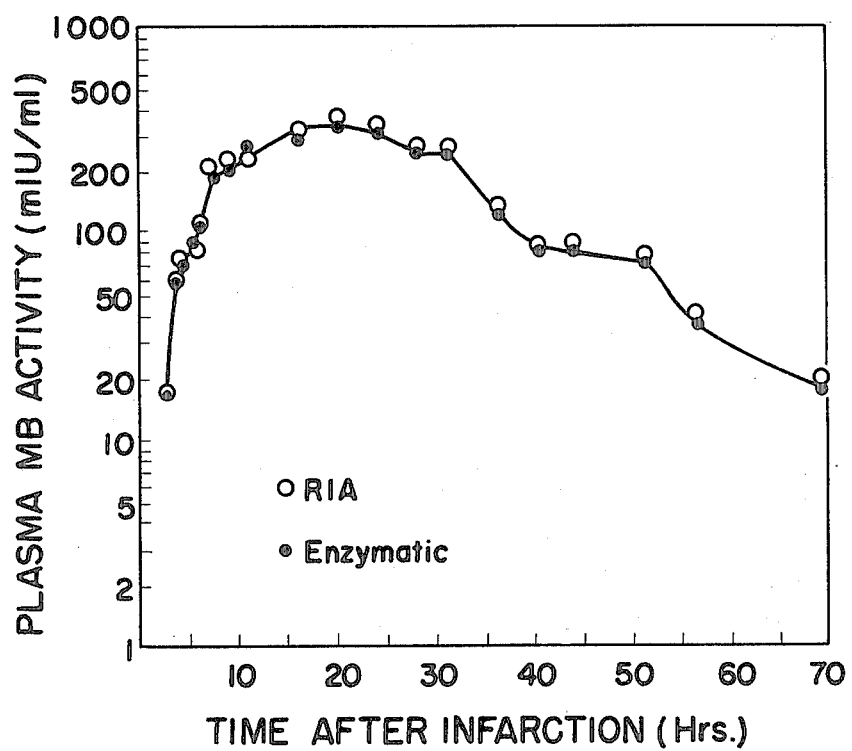

Results of samples obtained from five patients with acute myocardial infarction exhibited elevated MB CK in all cases. A typical MB CK curve from one of the patients is shown in FIG. 3 and demonstrates a high degree of correlation between activity-related and RIA analysis findings for a situation wherein the MB CK level is markedly elevated.

EXAMPLE 7

Typical Clinical Analysis for MB CK in a Plasma Sample

A. Materials

1. Five (5) vials, A-1, A-2, A-3, A-4 and A-5, are prepared with each containing the same known amount of $^{125}$I-labelled human BB CK.
2. Four (4) vials marked B-1, B-2, etc., are prepared with each containing unlabelled human MB CK with known amounts such that there would be a 100%, 60%, 40% and 20% inhibition of binding respectively (used to obtain the control standard inhibition curve).
3. Five (5) vials marked C-1, C-2, etc., are prepared with each containing the same known amount of human BB antiserum.
4. Six (6) vials marked D-1, D-2, etc., are prepared with each containing the same known amount of RIA-buffer (400 μl) containing 1.6 M Tris, 20 mM mercaptoethanol or other suitable reducing agent, 5 pg of rabbit gamma globin and 0.05% of bovine serum albumin at a pH of 7.4.

B. Methods

1. Vials C-1, C-2, C-3, C-4 are mixed with B-1, B-2, B-3, B-4 vials and D-1, D-2, D-3 and D-4 vials respectively and incubated for 30 minutes with gentle shaking at 4° C. and referred to as AB-1, AB-2, etc.
2. Following the above incubation steps, vials A-1, A-2, A-3, A-4 are added respectively to the appropriate AB vials (1, 2, 3, 4) and incubated for six (6) hours at 4° C. with gentle shaking.
3. Contemporaneously with steps 1 and 2, the C-5 vial is mixed with D-5 and 100 μl of plasma from the unknown sample and incubated for 30 minutes at 4° C. with gentle shaking after which it is added to A-5 vial and incubated for six (6) hours as above.
4. Following the six (6) hour incubation, 100 μl of saturated ammonium sulfate is added to all the tubes and incubated with gentle shaking for 15 minutes at 4° C.
5. All the tubes are centrifuged at 2000 g for 20 minutes.
6. Supernatant is discarded from all the tubes and 200 μl of buffer from D-6 tube is added for one washing and again supernatant is discarded.
7. The tubes containing the residue pellets are now put in the gamma counter and counted for radioactivity. The amount of binding present in vials 1-4 are plotted against the amount of CK present in vials marked B-1, B-2, etc. to obtain the standard inhibition reference curve. The amount of binding in the unknown plasma sample is placed on the curve and from the abscissa the amount of MB CK can be determined.

The above Examples have described a radioimmunoassay for CK isoenzymes. Antibodies were developed for MM and BB CK which are specific for the M and B subunits, respectively. Since MB CK, found in the human myocardium, contains both subunits, either antibody can be used to detect MB CK. The BB antibody reacts with BB and cross-reacts with MB CK, but not MM even when present in 5,000 molar excess over than of MB CK, a ratio far greater than that seen in plasma after myocardial infarction since MB CK is usually 10-15% of total CK activity. Detection of plasma MB CK using the BB system is specific for MB. Because BB CK activity is not present in normal plasma, even in patients with cerebral disorders or those with acute myocardial infarction, displacement binding reflects MB exclusively. This was corroborated by the close agreement (See, e.g., FIG. 3) between enzymatic activity determined by the kinetic fluorometric method and that obtained by the radioimmunoassay in samples obtained from patients with acute myocardial infarction.

The sensitivity provided by the assay (and illustrated in FIG. 2) is believed to exceed that of any prior assay by several fold. Present assays based on enzymatic activity can barely detect 0.010 IU/ml as opposed to the present assay which detects reliably 0.00001 IU/ml. Since mean plasma MB CK activity is 0.002 IU/ml, a five-fold increase is necessary for detection by enzymatic assays as opposed to the present assay which reliably detects any increase above normal. The increased sensitivity, coupled with its potential for detection of enzymatically inactive MB CK in the circulation should lead to improved estimates of infarct size as well as earlier detection of acute myocardial infarction. This is of particular importance in view of the recent enthusiasm for protection of ischemic myocardium in patients with acute myocardial infarction which demands a definitive diagnosis as soon as possible, since agents that can potentially decrease infarct size would be more effective if administered early.

The high level of specificity and sensitivity in the B subunit-containing CK isoenzyme radioimmunoassay system suggests that a similar approach may be useful in differentiation of other clinically important enzymes which exist in multiple forms. Studies evaluating the disappearance of other enzymes from the circulation have been restricted to determining the loss of activity. Because this assay detects the concentration of molecules, one can determine the actual rate of isoenzyme protein turnover independent of activity.

The assay should also help to elucidate mechanisms responsible for disappearance of individual CK isoenzymes from the circulation as well as aid in elucidating the relative importance of inactivation, denaturation, or removal of CK molecules under various clinical circumstances.

Numerous modifications and variations of the invention are expected to occur to those skilled in the art upon consideration of the foregoing detailed description. It can be anticipated that substantial variations in modes of securing BB CK antibodies, in labelling CK isoenzymes and in preparing suitable dissociation and polymerization-retarding buffers will be made. Consequently, only such limitations as appear in the appended claims should be placed upon the invention.

What is claimed is:

1. A competitive displacement radioimmunoassay method for quantitative determination of the concentration of a B subunit-containing isoenzyme of human creatine kinase in a sample, said method comprising:
    (1) incubating said sample with a pre-determined stoichiometric excess quantity of antibodies to purified BB creatine kinase to form a first reaction mixture comprising (a) the product of antigen-antibody association of B subunit-containing isoenzymes in the sample with antibodies to purified BB creatine kinase, and (b) unreacted antibodies to purified BB creatine kinase;
    (2) incubating the reaction mixture of step (1) with stoichiometric excess of radioisotopically labelled, purified B subunit-containing isoenzymes of creatine kinase to form a second reaction mixture comprising the association product of step (1) and the product of antigen-antibody association of said labelled isoenzymes with said unreacted antibodies in said first reaction mixture; and (3) removing unreacted labelled isoenzymes from said second reaction mixture and ascertaining the concentration of B subunit-containing isoenzymes in said sample on the basis of the extent of antigen-antibody association between said antibodies and said labelled isoenzyme.

2. The method of claim 1 wherein said antibody to purified BB creatine kinase is isolated from an animal immunized with purified BB creatine kinase.

3. The method of claim 1 wherein said radioisotopically labelled, purified B subunit-containing isoenzyme is BB isoenzyme.

4. A competitive displacement radioimmunoassay method for quantitative determination of the concentration of a B subunit-containing isoenzyme of human creatine kinase in a sample, said method comprising:

(1) incubating said sample in a medium having reducing agent activity with a pre-determined stoichiometric excess quantity of antibodies to purified BB creatine kinase to form a first reaction mixture comprising (a) the product of antigen-antibody association of B subunit-containing isoenzymes in the sample with antibodies to purified BB creatine kinase, and (b) unreacted antibodies to purified BB creatine kinase;

(2) incubating the reaction mixture of step (1) in a medium having reducing agent activity with a stoichiometric excess of radioisotopically labelled, purified B subunit-containing isoenzymes of creatine kinase to form a second reaction mixture comprising the association product of step (1) and the product of antigen-antibody association of said labelled isoenzymes with said unreacted antibodies in said first rection mixture, said labelled isoenzymes prepared by attaching a suitable radioisotopically labelled carrier molecule to the isoenzyme thus avoiding exposure of said isoenzyme to oxidative damage during labelling; and (3) removing unreacted labelled isoenzymes from said second reaction mixture and ascertaining the concentration of B subunit-containing isoenzymes in said sample on the basis of the extent of antigen-antibody association between said antibodies and said labelled isoenzyme.

5. The method of claim 4 wherein the medium wherein said incubation steps are carried out retards multiple reactions between antigen and antibody moieties and retards dissociation of the reacted moieties.

6. The method of claim 5 wherein said incubation steps are carried out in an aqueous buffer medium comprising Tris and having a pH of from 7.0 to about 8.0.

7. The method of claim 6 wherein the pH of said buffer is about 7.4.

8. The method of claim 5 wherein the radioisotopically labelled isoenzymes are labelled with $^{125}$I.

9. The method of claim 8 wherein said reducing agent is mercaptoethanol.

10. The method of claim 4 wherein the medium wherein said incubation steps are carried out is an aqueous buffer having a pH of about 7.4 and comprising Tris, gamma globulin, serum albumin and mercaptoethanol.

11. A combination of reagents for use in the quantitative detection, by radioimmunoassay of the concentration of a B subunit-containing isoenzyme of creatine kinase in a sample, said combination of reagents comprising:

(1) a pre-determined quantity of an antibody to purified BB creatine kinase, reactive with B subunit-containing isoenzymes of creatine kinase to form an antigen-antibody association upon contact therewith and being substantially unreative with MM creatine kinase; and (2) a pre-determined quantity of a radioisotopically labelled, purified B subunit-containing isoenzyme of creatine kinase, capable of antigen-antibody association with said antibody upon contact therewith, said labelled isoenzymes prepared by attaching a suitable radioisotopically labelled carrier molecule to the isoenzymes thus avoiding exposure of said isoenzyme to oxidative damage.

12. A combination of reagents in claim 11 further including a medium which has reducing agent activity and which retards multiple reactions between the antigen and antibody moieties and which retards dissociation of the reacted moieties.

13. A combination of reagents as set forth in claim 12 wherein the medium is an aqueous buffer solution having a pH of about 7.4 comprising Tris, gamma globulin, serum albumin and mercaptoethanol.

14. A combination of reagents as set forth in claim 11 wherein said radioisotopically labelled, purified isoenzyme is an acylation product of the reaction of purified isoenzyme with iodinated N-succinimidyl-3-(4-hydroxphenyl propionate).

15. A combination of reagents as set forth in claim 11 wherein said radioisotopically labelled, purified isoenzyme is BB isoenzyme.

* * * * *